(12) United States Patent
Kesling et al.

(10) Patent No.: US 6,786,720 B1
(45) Date of Patent: Sep. 7, 2004

(54) EPOXY RESIN BONDING PAD FOR A CERAMIC ORTHODONTIC APPLIANCE

(75) Inventors: Andrew C. Kesling, LaPorte, IN (US); Thrumal Devanathan, Warsaw, IN (US)

(73) Assignee: TP Orthodontics, Inc., Westville, IN (US)

( * ) Notice: Subject to any disclaimer, the term of this patent is extended or adjusted under 35 U.S.C. 154(b) by 203 days.

(21) Appl. No.: 10/120,052

(22) Filed: Apr. 10, 2002

(51) Int. Cl.[7] .................................................. A61C 3/00
(52) U.S. Cl. ............................................................ 433/9
(58) Field of Search .............................. 433/3, 4, 9, 24

(56) References Cited

U.S. PATENT DOCUMENTS

| | | | |
|---|---|---|---|
| 4,695,508 | * | 9/1987 | Kageyama et al. ......... 442/149 |
| 4,739,002 | * | 4/1988 | Ishikawa et al. ............ 524/270 |
| 4,954,080 | | 9/1990 | Kelly et al. |
| 5,098,288 | | 3/1992 | Kesling |
| 5,263,859 | | 11/1993 | Kesling |

FOREIGN PATENT DOCUMENTS

| | | |
|---|---|---|
| EP | 1 352 617 A1 * | 10/2003 |
| GB | 2247685 A | 3/1992 |
| WO | WO 97/41796 | 11/1997 |

OTHER PUBLICATIONS

Derwent Publications Ltd. Database No. XP 002246736.

* cited by examiner

Primary Examiner—Ralph A. Lewis
(74) Attorney, Agent, or Firm—Lloyd L. Zickert

(57) ABSTRACT

A light-curable methacrylate based epoxy resin bonding pad molded to a ceramic orthodontic appliance, wherein the epoxy resin is made of bisphenol glycidyl methacrylate, tetra-hydrofurfuryl methacrylate, titanium dioxide, and camphor quinone, and the invisible light transmittance through the appliance and the pad is on the order of five percent plus or minus two percent.

16 Claims, 2 Drawing Sheets

EPOXY RESIN BONDING PAD FOR A CERAMIC ORTHODONTIC APPLIANCE

This invention relates in general to an epoxy resin bonding pad for a ceramic orthodontic appliance, and more particularly to a light-curable methacrylate based epoxy resin bonding pad molded onto a ceramic orthodontic bracket.

BACKGROUND OF THE INVENTION

Heretofore, it has been known to provide flexible bonding pads for ceramic brackets to facilitate debonding of the bracket or appliance from a tooth without causing damage to the enamel of the tooth and/or breakage of the bracket, as disclosed in U.S. Pat. No. 5,098,288 and 5,263,859.

It has also been known to mold an epoxy resin bonding pad onto a ceramic bracket wherein the epoxy resin is heat-cured. The transmittance of visible light through this bracket and pad is on the order of twenty percent Such bonding pads have textured surfaces for enabling the mechanical adhesive bonding of the bracket and pad to a tooth. This epoxy resin is a two-component system which requires heat-curing.

SUMMARY OF THE INVENTION

The present invention relates to an improved epoxy resin for making the bonding pads of ceramic orthodontic appliances such as brackets, wherein the improved resin is used for casting the bonding base onto the ceramic appliance. The bonding pad of the invention is formed from a light-curable resin that contains a metallic oxide and results in a better match of tooth color and improved bond strength.

The improved resin is acrylic based and is compounded with suitable monomers and light-curing catalysts, together with a metal oxide pigment. Accordingly, the improved resin according to the invention, when cast or molded onto a ceramic orthodontic appliance is light cured.

The light-cured resin cast bonding pad of the invention enables the mechanical bonding of the bracket to a tooth and which can be debonded without use of special tools, without damaging the tooth enamel, and without causing breakage of the ceramic bracket. Debonding is performed by squeezing the pad with ligature cutters causing the bracket to release from the tooth.

It is therefore an object of the present invention to provide a new and improved acrylic based epoxy resin for casting bonding pads onto ceramic orthodontic appliances.

A further object of the present invention is to provide a new and improved bonding pad or base for orthodontic ceramic appliances which increases the bond strength and more closely matches the tooth color by decreasing the transmittance of visible light through the bracket and pad.

A still further object of the present invention is to provide an improved epoxy resin for casting bonding pads onto orthodontic ceramic brackets that is light-curable.

Other objects, features and advantages of the invention will be apparent from the following detailed disclosure, taken in conjunction with the accompanying sheets of drawings, wherein like reference numerals refer to like parts.

DESCRIPTION OF THE INVENTION

The improved epoxy resin of the invention for casting a bonding base or pad onto a ceramic orthodontic appliance is light-curable and contains a metallic oxide having pigment characteristics that causes the bracket and pad to more closely match the tooth color than prior known appliances with epoxy resin bonding pads.

The epoxy resin of the invention is acrylic based and compounded from bisphenol glycidyl methacrylate, tetra-hydrofurfuryl methacrylate, titanium dioxide, and camphor quinone. The resin requires approximately thirty seconds to cure under a blue light source having a nominal range of 460 to 490 nanometers (nm). The percentage by weight of the components in a batch blend is as follows:

TABLE I

| | |
|---|---|
| Bisphenol glycidyl methacrylate | 50% |
| Tetra-hydrofurfuryl methacrylate | 48% |
| Titanium dioxide | 0.5% |
| Camphor quinone (catalyst) | 1.5% |
| Total | 100% |

It will be appreciated that the percent-by-weight values of the elements in Table I may be varied plus or minus ten percent and still be within the scope of the invention.

The camphor quinone is a 470 nm system for making the compound light-curable, and it should be appreciated that other systems could be used, if desired. This system allows the resin to be cured under a blue light source covering a spectral value in the range of about 460 to 490 nm, in approximately thirty seconds.

Brackets of polycrystalline alumina oxide with a bonding base or pad as formulated in accordance with Table I were bonded onto a test plate of a Tensil tester and tested for bond strength. The pad included a textured surface and was mechanically bonded to the test plate by a mechanical bond adhesive. Similarly, brackets with the same resin except without titanium dioxide were tested. The bond strength evaluation for the brackets is set forth in the following table.

TABLE II

| Resin Type | Bond Strength (pounds) |
|---|---|
| Light-cure resin without $TiO_2$ | 43 |
| Light-cure resin with $TiO_2$ | 51 |

Accordingly, it was determined that the light-cure resin with titanium dioxide produced a nineteen percent higher bond strength than without the resin.

Figure 1:
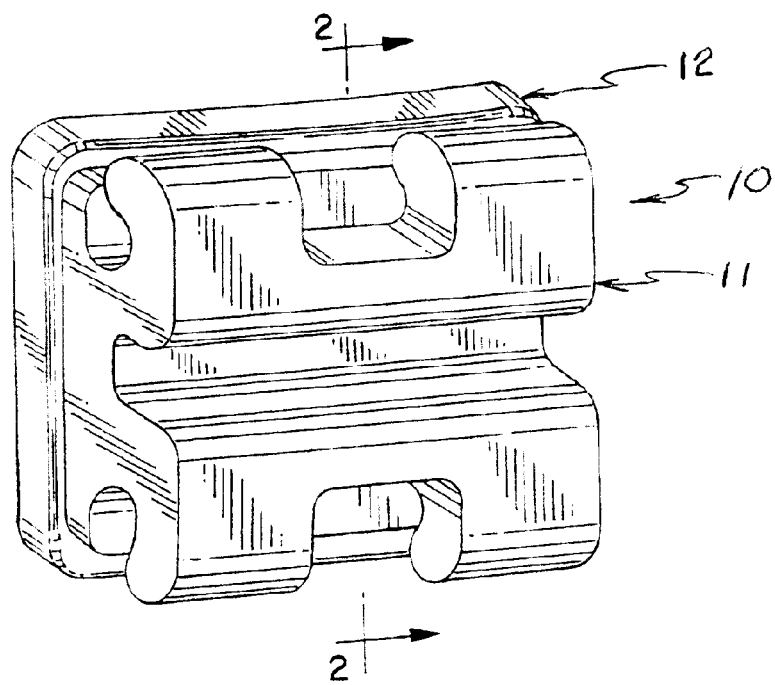
FIG. 1 is a perspective view of a ceramic orthodontic bracket having the epoxy resin bonding pad according to the invention.
Figure 2:
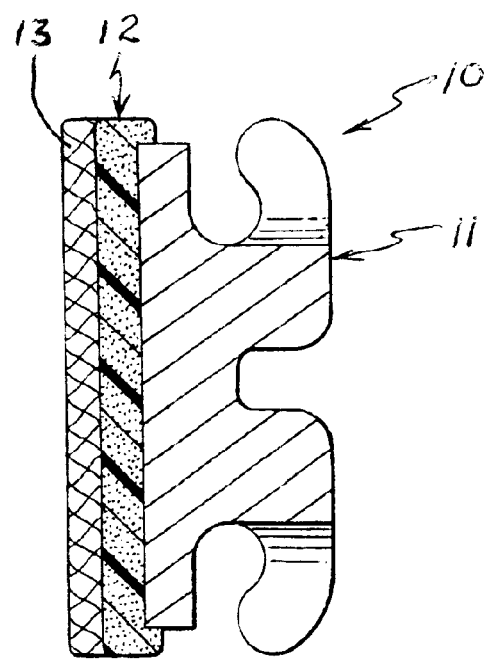
FIG. 2 is a vertical sectional view taken through the bracket and bonding pad of FIG. 1, and substantially along line 2—2 thereof.

A combination ceramic orthodontic bracket and bonding pad is shown in FIGS. 1 and 2 and generally indicated by the numeral 10, and includes a polycrystalline ceramic bracket 11 with an acrylic based epoxy resin bonding pad 12 according to the invention cast onto the bracket. The bracket may be made by any suitable way, such as by injection molding ceramic material and sintering, or by machining from a bar of ceramic. The bonding surface 13 of the pad is suitably textured to enhance a mechanical adhesive bonding with a tooth. Any suitable adhesive may be used to bond the bracket to the tooth, such as those sold by TP Orthodontics, Inc. of LaPorte, Ind., U.S.A., and recommended for bonding ceramic brackets to teeth, including a light cure bonding adhesive.

In order for the color of the bracket to be matched more closely to the enamel of the tooth, the majority of the visible light traveling through the bracket and the epoxy resin bonding pad cannot be transmitted.

The heat-cured epoxy resin bonding pad of the prior art produces a light transmittance of the visible light between 380 and 760 nm on the order of twenty percent.

Figure 3:
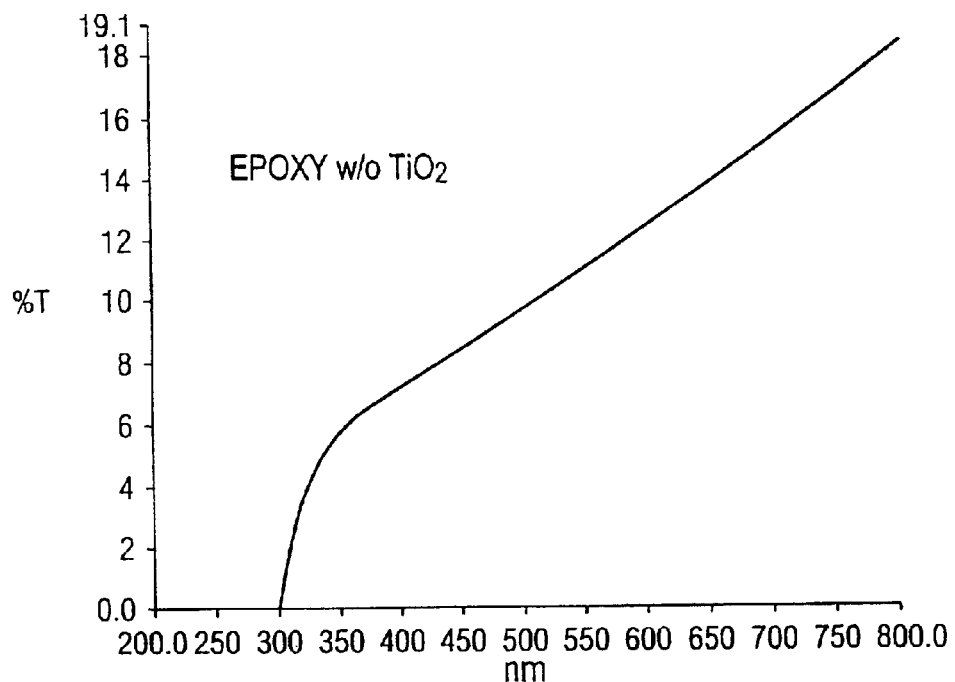
FIG. 3 is a graphical illustration of the transmittance of visible light through an orthodontic ceramic bracket having an epoxy resin bonding pad without titanium dioxide.
Figure 4:
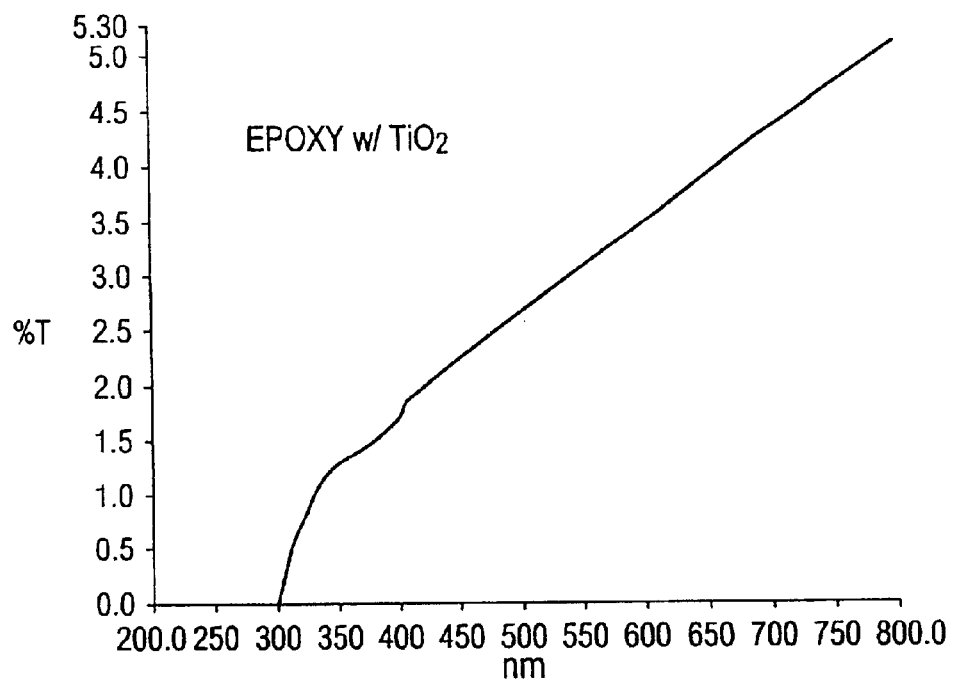
FIG. 4 is a graphical illustration of the transmittance of visible light through an orthodontic ceramic bracket having an epoxy resin bonding pad with titanium dioxide according to the present invention.

For producing a comparison between a light cure epoxy resin cast on a ceramic bracket with and without a pigmented metallic oxide, batches were prepared without titanium dioxide and with titanium dioxide and each cast on a bracket and tested for light transmittance, as illustrated in FIGS. 3 and 4. The abscissas or horizontal coordinates of the graphs represent wave energy in nanometers (nm) from 200.0 to 800.0, where the range of about 380 nm to 760 nm is considered the visible light spectrum, while the ordinates or vertical coordinates represent percent of light transmittance (%T). Thus, the percent of visible light transmittance at 300 nm is zero in both graphs.

The bracket with the epoxy resin of the invention which includes titanium dioxide of about 0.5 percent by weight, as shown in FIG. 4, produced a visible light transmittance of about 1.5 percent to 4.8 percent, while the bracket cast with epoxy resin without titanium dioxide, as shown in FIG. 3, produced a visible light transmittance of about 7.0 to 17.0 percent. The visible light transmittance at 470 nm is about 2.5 percent for the bracket with resin having titanium dioxide, as seen in FIG. 4, while the visible light transmittance of the bracket with epoxy resin without the titanium dioxide is about 9.0 percent, as seen in FIG. 3. Depending on the preciseness of measuring the components for the epoxy resin, the light transmittance values will be plus or minus about two percent.

Further, the effect of adding titanium dioxide produced a resin of greater viscosity. Using a Brookfield viscometer, the resin with the titanium dioxide had an increased viscosity over the resin without the titanium dioxide, as follows:

TABLE III

| Resin Type | Viscosity Measurement in centipoises (cps) |
| --- | --- |
| The epoxy resin with titanium dioxide | 700 |
| The epoxy resin without titanium dioxide | 660 |

The measurements were taken with resin at a temperature of about 63 degrees F. and utilizing a revolutions per minute of 20 on a No. 2 spindle.

In view of the foregoing, it should be appreciated that the titanium dioxide filled light-curable acrylic-based epoxy resin of the present invention produces a bonding pad for a polycrystalline ceramic orthodontic bracket having greater bond strength and also a better tooth color because the transmittance of visible light has been materially lowered.

It will be understood that modifications and variations may be effected without departing from the scope of the novel concepts of the present invention, but it is understood that this application is to be limited only by the scope of the appended claims.

What is claimed is:

1. In combination with a ceramic orthodontic appliance, an acrylic based epoxy resin bonding base molded onto the lingual side of the appliance, said epoxy resin comprising 50 percent by weight bisphenol glycidyl methacrylate, 48 percent by weight tetra-hydrofurfuryl methacrylate, 0.5 percent by weight titanium dioxide, and 1.5 percent by weight catalyst, said percent by weight values ranging plus or minus ten percent.

2. The combination defined in claim 1, wherein the catalyst is camphor quinone.

3. The combination defined in claim 1, wherein said resin is light-curable.

4. The combination defined in claim 1, wherein said appliance is a bracket.

5. The combination defined in claim 1, wherein the visible light transmittance through the appliance and the bonding pad is less than about five percent, plus or minus about two percent.

6. The combination defined in claim 1, wherein the appliance is of polycrystalline alumina oxide.

7. A polycrystalline ceramic orthodontic appliance having an acrylic modified light-cured epoxy resin bonding base molded to the appliance for mounting the appliance to a tooth, said epoxy bonding base comprising by weight: about 50 percent bisphenol glycidyl methacrylate, about 48 percent tetra-hydrofurfuryl methacrylate, about 0.5 percent light-blocking oxide pigment, and about 1.5 percent catalyst.

8. The appliance of claim 7, wherein the light-blocking pigment is titanium dioxide.

9. The appliance of claim 8, wherein the catalyst is camphor quinone.

10. The appliance of claim 9, wherein the bonding base is light-cured onto the appliance.

11. The appliance of claim 7, wherein the visible light transmittance through the appliance and the bonding pad is about five percent, plus or minus about two percent.

12. An acrylic light-curable epoxy resin bonding pad for molding onto a ceramic orthodontic bracket comprising by weight: about 50 percent bisphenol glycidyl methacrylate, about 48 percent tetra-hydrofurfuryl methacrylate, about 0.5 percent light-blocking oxide pigment, and about 1.5 percent catalyst, said percent by weight values ranging plus or minus ten percent.

13. The resin of claim 12, wherein the light-blocking oxide pigment is titanium dioxide.

14. The resin of claim 13, wherein the catalyst is camphor quinine.

15. The resin of claim 14, wherein the visible light transmittance through the bracket and the bonding pad is about five percent, plus or minus about two percent.

16. The method of mounting an acrylic epoxy resin bonding pad to a ceramic othodonic appliance, said method comprising preparing the epoxy resin by combining by weight about 50 percent bisphenol glycidal methacrylate, about 48 percent tetra-hydrafurfuryl methacrylate, about 0.5 percent titanium dioxide, and about 1.5 percent camphor quinone, said percent by weight values ranging plus or minus ten percent, depositing the epoxy resin in a mold, setting an appliance in the resin, and subjecting the resin to a curing light to cure the resin.

* * * * *